United States Patent [19]

Harris et al.

[11] 4,242,284
[45] Dec. 30, 1980

[54] PROCESS FOR RECOVERY OF RHODIUM VALUES AND TRIPHENYLPHOSPHINE FROM RHODIUM CATALYZED HYDROFORMYLATION MEDIUM

[75] Inventors: Norman Harris; Thomas F. Shevels, both of Stockton-on-Tees, England

[73] Assignee: Davy International (Oil & Chemicals) Limited, London, England

[21] Appl. No.: 60,754

[22] Filed: Jul. 26, 1979

[30] Foreign Application Priority Data

Jul. 27, 1978 [GB] United Kingdom ............... 31366/78

[51] Int. Cl.³ ............................................. C07C 45/50
[52] U.S. Cl. .................................................. 568/454
[58] Field of Search ................. 260/604 HF; 252/413, 252/429

[56] References Cited

U.S. PATENT DOCUMENTS

| | | | |
|---|---|---|---|
| 3,527,809 | 9/1970 | Pruett et al. .................. | 260/604 HF |
| 3,547,964 | 12/1970 | Olivier ......................... | 260/604 HF |
| 3,641,076 | 2/1972 | Booth ............................ | 260/604 HF |
| 3,857,895 | 12/1974 | Booth ............................ | 260/604 HF |
| 4,113,754 | 9/1978 | Kummer et al. ............... | 260/604 HF |

FOREIGN PATENT DOCUMENTS

1338237 11/1973 United Kingdom ............. 260/604 HF

OTHER PUBLICATIONS

"Elements of Physical Chemistry" 2nd. ed. Glasstone and Lewis pp. 520–527 (52b).

*Primary Examiner*—Werren B. Lone
*Attorney, Agent, or Firm*—Bernard & Brown

[57] ABSTRACT

A hydroformylation process is disclosed utilizing a rhodium complex catalyst and an excess of a triorganophosphine wherein active rhodium catalyst and triorganophosphine can be separated from inactive rhodium, "heavies" and triorganophosphine oxide in partially deactivated reaction medium by extraction into concentrated phosphoric acid or aqueous solutions containing at least 40% by weight phosphoric acid. By neutralization of the phosphoric acid extract in the presence of organic solvent, e.g. aldehyde trimers, a solution of active rhodium catalyst and triorganophosphine can be produced that is suitable for re-use in the hydroformylation reaction.

9 Claims, 1 Drawing Figure

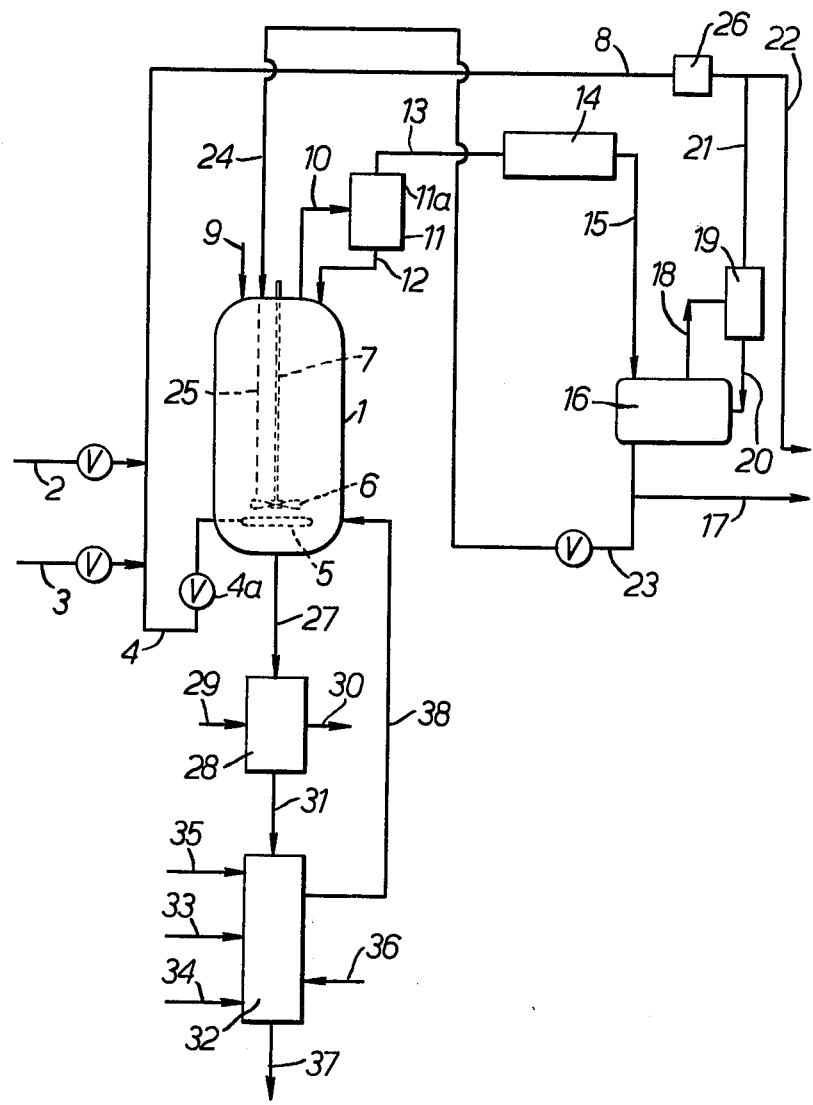

PROCESS FOR RECOVERY OF RHODIUM VALUES AND TRIPHENYLPHOSPHINE FROM RHODIUM CATALYZED HYDROFORMYLATION MEDIUM

PROCESS

This invention relates to hydroformylation, more particularly to hydroformylation of an α-olefinic compound to produce an aldehydic compound containing one more carbon atom than the α-olefinic compound.

Hydroformylation is a well-known process involving reaction of a 1:1 $H_2:CO$ mixture with the α-olefinic compound, e.g. an α-olefin, in the presence of a suitable catalyst and under appropriate temperature and pressure conditions. Although ethylene gives a single product, i.e. propionaldehyde, for $C_3$ and higher olefins the product is usually a mixture of aldehydes, thus:

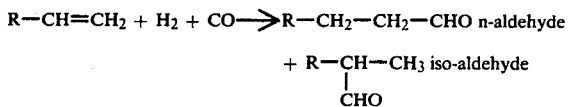

Normally the n-isomer is of greater commercial value than the i-aldehyde. Hence, in the hydroformylation of $C_3$ and higher olefins, production of high n-/i- ratios is desirable.

Hydroformylation is not restricted to α-olefins and proposals have been made to hydroformylate other α-olefinic compounds such as allyl alcohol, allyl acetate and vinyl acetate.

Although the catalysts used in the first commercial hydroformylation plants were based on cobalt, these required operation at extremely high pressure and separation of the product from the cobalt carbonyls used as catalyst proved difficult. Furthermore the n-/i- ratio was generally no higher than about 4:1.

More recently a rhodium catalysed hydroformylation process has been commercially adopted. This is described, for example, in an article entitled "Low-pressure OXO process yields a better product mix," Chemical Engineering, Dec. 5, 1977. A further description of the process can be obtained, for example, from U.S. Pat. No. 3,527,809 and British Pat. No. 1338237. Besides the fact that this rhodium-catalysed process permits n-/i-ratios of 10:1 or higher to be obtained, the gas recycle flow sheet utilised provides a simple method for recovering product aldehyde, since the rhodium complex catalyst is non-volatile. In addition operation can be effected at much lower pressures and at lower temperatures than are used in cobalt-catalysed hydroformylation plants.

In this rhodium catalysed hydroformylation process the reaction takes place in a liquid reaction medium which contains a soluble rhodium complex catalyst which comprises rhodium in complex combination with carbon monoxide and a triorganophosphine ligand, typically a triarylphosphine such as triphenylphosphine. The active catalytic species is believed to be hydridocarbonyl tris(triphenylphosphine) rhodium (I), $H(CO)Rh(TPP)_3$ wherein $TPP=(C_6H_5)_3P$. In addition to the rhodium complex catalyst the reaction medium comprises excess triorganophosphine ligand, product aldehyde and polymeric aldehyde condensation products.

Commercial experience has shown that the rhodium complex catalyst may be deactivated by the presence in the feedstock of extrinsic catalyst poisons, such as sulphurous compounds (e.g. $H_2S$, COS and $CH_3SH$) or halogen compounds (e.g. HCl), which can react with the rhodium of the catalyst to form inactive species containing, for example, Rh-S or Rh-halogen bonds which are not destroyed under the mild hydroformylation conditions employed. Hence extreme care is taken to purify the feedstocks. However, even using rigorously purified feedstocks, some intrinsic deactivation of the catalyst may occur. The reasons for such deactivation are not entirely clear but it is thought that inactive species containing Rh—Rh bonds may be formed. In addition oxidation of triphenylphosphine to the corresponding oxide may occur due to traces of oxygen in the feedstocks.

In present day commercial plants it is usual to operate the process for perhaps upwards of 1 year during which time any decline in catalyst activity is offset by addition of fresh catalyst or catalyst precursor, e.g. rhodium carbonyl triphenylphosphine acetylacetonate or rhodium dicarbonyl acetylacetonate, together with fresh triorganophosphine ligand. Eventually, however, the levels of deactivated rhodium species and of triphenylphosphine oxide may rise to undesirable values whereupon it becomes expedient to replace the catalyst charge completely, even though this still contains a significant proportion of active rhodium complex catalyst. Because rhodium is an expensive metal it is uneconomic to discard the spent catalyst and the usual practice is for this to be returned to the catalyst manufacturer for recovery of rhodium from which fresh catalyst or catalyst precursor can be produced. Since the catalyst is not reprocessed at the plant this means that the manufacturer must purchase a sufficient inventory of catalyst to enable him to continue operation whilst a catalyst charge is being reprocessed. Because of the high cost of rhodium the catalyst inventory will usually represent a significant capital investment.

In the existing commercial plants for producing propionaldehyde from ethylene and butyraldehyde from propylene a gas recycle system is utilised to remove product aldehyde and also aldehyde condensation products, such as trimers, in the vapour phase from the liquid rhodium complex catalyst-containing reaction medium in the hydroformylation reactor at the rate at which they are formed. Although this procedure is quite satisfactory when utilising ethylene or propylene as a feedstock, the use of $C_4$ and higher α-olefins presents somewhat of a problem in that the product aldehydes and their polymeric condensation products are less volatile than the corresponding products and by-products of the hydroformylation of ethylene or propylene. Although this lesser volatility can be compensated for, at least to some extent, by increasing the gas recycle rate, this requires the use of a larger gas recycle compressor which adds significantly to the capital cost of the plant.

There is thus a need for a process which will permit, by the use of simple techniques which can be adopted on the production plant, recovery of active rhodium catalyst from the liquid reaction medium used in the hydroformylation reactor. There is also a need to provide a process which does not rely wholly on gas recycle for removal of "heavies," i.e. polymeric aldehydic condensation products, and by which the control of "heavies" in the reaction medium can be achieved in a simple manner.

It is accordingly an object of the present invention to provide a process whereby active rhodium complex catalyst and triorganophosphine ligand can be recovered from constituents of a liquid hydroformylation reaction medium and simultaneously separated from catalytically inactive rhodium species and from "heavies."

According to the present invention there is provided a process for hydroformylating an α-olefinic compound to produce an aldehydic compound or a mixture of aldehydic compounds having one more carbon atom than the α-olefinic compound which comprises:

reacting the α-olefinic compound in a hydroformylation zone with carbon monoxide and hydrogen in a liquid reaction medium which contains a soluble rhodium complex catalyst comprising rhodium in complex combination with carbon monoxide and a triorganophosphine ligand and in the presence of excess triorganophosphine ligand;

contacting constituents of the liquid reaction medium with a liquid extractant phase comprising at least about 40% by weight phosphoric acid;

separating an organic phase now depleted in rhodium and triorganophosphine ligand from extractant phase;

recovering rhodium values and triorganophosphine ligand from separated extractant phase; and recycling at least one of recovered rhodium values and recovered triorganophosphine ligand to the hydroformylation zone.

The ability to extract selectively the active catalytic rhodium species and triorganophosphine ligand from the constituents of the liquid hydroformylation reaction medium appears to be specific to concentrated phosphoric acid and strong aqueous solutions thereof. Experiments with other acids such as acetic acid, phthalic acid, glycine, p-toluenesulphonic acid, and iso-butyric acid failed to yield a satisfactory extraction procedure; with these other acids rhodium and ligand were not extracted into an aqueous layer.

In the process of the invention there is contemplated the use of α-olefins as well as compounds contaning α-olefinic groups. Typically such α-olefinic compounds contain from 2 to about 20 carbon atoms or more. Typical α-olfins include ethylene, propylene, butene-1, pentene-1, hexene-1, heptene-1, octene-1, nonene-1, decene-1, and their homologues, as well as isomers thereof, such as 3-methylbutene-1, iso-propylethylene, 2-ethylhexene-1, iso-octene, and 2-methylbutene-1, and the like. Aromatic olefins such as styrene and allyl benzene, and terpenes, such as myrcene and d-limonene can also be contemplated for use in the process of the invention. Typical α-olefinically substituted compounds include allyl alcohol, allyl acetate, vinyl acetate, diallyl ether, and the like.

Hydroformylation is effected in the liquid reaction medium in the presence of a catalytically effective amount of the rhodium complex catalyst. Typically the rhodium complex catalyst concentration ranges from about 20 parts per million, calculated as rhodium metal, up to about 1000 parts per million or more. There is no advantage generally in using concentrations of rhodium in excess of about 500 parts per million and usually, on the grounds of expense alone, it will be preferred to operate at a rhodium complex catalyst concentration of not more than about 300 parts per million, calculated as rhodium metal. Typically operating conditions utilise rhodium complex catalyst concentrations of from about 50 parts per million up to about 150 parts per million, calculated as rhodium metal.

The triorganophosphine ligand may be an aliphatic phosphine, such as tributyl phosphine, but is preferably an aromatic phosphine, such as triphenylphosphine, tri-(p-methoxyphenyl) phosphine, trinaphthylphosphine, tritolylphosphine, p-N,N-dimethylaminophenyl diphenylphosphine, and the like. The preferred ligand is triphenylphosphine. During the course of hydroformylation utilising a rhodium complex catalyst small quantities of alkyl diphenylphosphines may be formed by interaction between the ligand and the α-olefinic compound in the presence of the rhodium complex catalyst. Thus, when hydroformylating propylene, for example, small amounts of propyl diphenyl phosphine may be formed as by-product.

The liquid reaction medium contains excess triorganophosphine ligand. Preferably there are at least about 2 moles of free ligand for every gram atom of rhodium present. Usually it will be preferred to operate in the presence of at least 10 moles of free ligand, typically in the presence of at least 75 moles, for example at least 100 moles, of free triorganophosphine ligand per gram atom of rhodium. The upper limit of the amount of free triorganophosphine ligand is not particularly critical and is dictated by the solubility thereof in the liquid reaction medium, as well as be economic and commercial considerations. Although not so expensive as the rhodium inventory, the capital cost of the triphenylphosphine inventory is a significant factor. Under typical operating conditions the free triorganophosphine ligand constitutes from about 2% to about 25% by weight of the liquid reaction medium.

The rhodium complex catalyst may be formed by methods known in the art. For example, hydridocarbonyl tris(triphenylphosphine) rhodium (I) is a crystalline solid and may be introduced into the hydroformylation reactor as such. Alternatively a catalyst precursor, such as rhodium carbonyl triphenylphosphine acetylacetonate or rhodium dicarbonyl acetylacetonate may be introduced into the reactor and the active catalytic species, believed to be hydridocarbonyl tris(triphenylphoshine) rhodium (I) generated in situ under hydroformylation conditions in the presence of excess triphenylphosphine. Other suitable precursors include $Rh_2O_3$, $Rh_4(CO)_{12}$ and $Rh_6(CO)_{16}$.

The liquid reaction medium further includes aldehydic product and polymeric aldehyde condensation products. The nature of such polymeric condensation products (e.g. dimers, trimers, and tetramers) and a postulated mechanism for their formation are discussed in British Pat. No. 1338237 to which further reference should be made. Analogous condensation products are formed to those described at page 3 line 19 to page 5 line 25 of British Pat. No. 1338237 when utilising α-olefinic compounds other than propylene as feedstock in the process of the present invention.

The ratio of aldehyde to polymeric aldehydic condensation products in the liquid reaction mixture may vary within wide limits. Typically this ratio lies in the range of from about 1:4 to about 4:1 by weight, e.g. about 1:1 by weight.

In the hydroformylation zone conditions are maintained which are effective for hydroformylation of the α-olefinic compound. Typically the temperature lies in the range of from about 50° C. up to about 160° C. or more. The temperature should be at least as high as that required to effect hydroformylation but not so high as to destroy the catalyst. Usually the temperature will lie in the range of from about 70° C. to about 140° C., e.g. in the range of from about 90° C. to about 130° C.

The total pressure in the hydroformylation zone will usually be about 50 kg/cm$^2$ absolute or less and is preferably less than about 20 kg/cm$^2$ absolute. Typically the partial pressure attributable to the α-olefinic compound is less than about 1.5 kg/cm$^2$. The total partial pressure attributable to hydrogen and carbon monoxide is typically less than about 30 kg/cm$^2$. Usually the carbon monoxide partial pressure is 1.5 kg/cm$^2$ or less whilst the hydrogen partial pressure preferably lies in the range of from about 1.5 kg/cm$^2$ to about 7.5 kg/cm$^2$.

Particularly when using a C$_2$ to C$_5$ olefin as the α-olefinic compound, the process may be operated using the gas recycle system described in West German Offenlegungsschrift No. 2715685.

In the process of the invention, as a result of the presence of extrinsic catalyst poisons in the feedstocks supplied to the hydroformylation reactor and/or as a result of intrinsic catalyst poisoning due to interaction between the catalyst and itself or one or more of the other constituents of the liquid reaction medium, at least some conversion of active catalyst species to inactive rhodium species may occur. Furthermore undesirable amounts of triorganophosphine oxide may be formed, e.g. as a result of trace amounts of molecular oxygen in one of the feedstocks. Such oxygen may arise, for example, by reason of addition of small amounts of oxygen to the synthesis gas during purification in order to destroy metal carbonyls. Other undesirable by-products may include substituted phosphines formed by interaction between the α-olefinic compound and the catalyst or the ligand, as for example propyldiphenylphosphine which is formed as by-product in the hydroformylation of propylene. "Heavies," i.e. polymeric aldehyde condensation products, may also build up to undesirable levels in the liquid reaction medium. Accordingly the process envisages that constituents of the liquid reaction medium are contacted with an extractant so as to recover therefrom active rhodium complex catalyst and free ligand in high yield.

The extraction step may be performed upon a portion of, or upon the whole of, the liquid reaction medium without any pretreatment step. Extraction may thus be operated batchwise on a part of, or on the whole of, the charge of liquid reaction medium in the hydroformylation reactor. For this purpose the liquid reaction medium to be extracted can be withdrawn from the reactor or hydroformylation can be interrupted whilst treatment takes place. Alternatively the extraction step can be effected continuously by treating a bleed stream from the reactor. If the aldehydic product is water soluble, product recovery may include a water wash step. In this case the extraction step can be carried out subsequent to product recovery.

Prior to extraction the liquid reaction medium can be subjected to a suitable pretreatment for stripping α-olefinic compound, aldehydic product and/or "heavies" therefrom. In the case where the aldehydic product and/or "heavies" is or are water-soluble, such pretreatment may involve a water washing step. In the event that the α-olefinic compound, aldehydic product and/or "heavies" is or are volatile, the liquid reaction medium can be subjected to a suitable pretreatment for removal of the volatile component(s), as for example by heating, subjection to vacuum, or passage of an inert gas therethrough or to a combination of two or more of these techniques. In some cases extraction may be improved by addition of an inert solvent, preferably a non-polar solvent, to the optionally pretreated liquid reaction medium. Typical inert solvents include hexane, heptane, benzene, toluene, and xylene.

The liquid reaction medium, optionally after a pretreatment step such as is described in the preceding paragraph or after addition of an inert solvent, is contacted with a liquid extractant phase comprising phosphoric acid. Orthophosphoric acid, preferably so-called "food grade" phosphoric acid, can be used as well as concentrated aqueous solutions thereof. "Superphosphoric acid" which contains mixtures of orthophosphoric acid, pyrophosphoric acid and higher polymers, can also be used but is less preferred. As well as concentrated phosphoric acid there can be used aqueous phosphoric acid solutions containing at least about 40% by weight phosphoric acid, preferably at at least about 60% by weight phosphoric acid up to 80% by weight or more, which are preferably pre-saturated with product aldehyde(s).

In this extraction step the liquid reaction medium is intimately mixed with the extractant. Any suitable mixing apparatus can be used. The mixed phases are then allowed to separate and the phosphoric acid extractant phase is drawn off. Hence the process can be effected in conventional mixer-settler equipment.

The separated phosphoric acid extractant phase is found to contain a major part of the catalytically active rhodium present in the liquid reaction medium immediately prior to extraction and a major part of the free triorganophosphorus ligand. Although it is not desired to be bound by the following explanation, it is believed that the rhodium catalytic species becomes protonated by the phosphoric acid, thereby forming a salt that is soluble in phosphoric acid as well as in water and in aqueous phosphoric acid solutions, the anion of which salt is derived from the phosphoric acid, whilst the triorganophosphine ligand, as well as any by-product phosphine (as, for example, propyldiphenylphosphine formed as by-product in the hydroformylation of propylene), dissolves as a salt in the phosphoric acid layer; on the other hand any water-insoluble impurities, such as catalytically inactive rhodium species, triphenylphosphine oxide, or "heavies," remain dissolved in the organic layer.

Extraction can be effected with concentrated phosphoric acid; in this case the resulting separated extractant phase is diluted somewhat with water for further work-up. Alternatively extraction can be effected with a concentrated aqueous phosphoric acid solution.

Following extraction the extractant phase is further worked up in order to recover the extracted catalytically active rhodium species and triorganophosphorus ligand. Typically such a further work-up involves neutralisation with a base, optionally after dilution with water. It is preferred to neutralise in the presence of an organic solvent for the active catalytic rhodium species and for the triorganophosphorus ligand. In this way an organic solution is obtained which can be returned directly to the hydroformylation reactor. By appropriate careful pH control during neutralisation at least partial separation of the desired free ligand, e.g. triphenylphosphine, from any by-product phosphine present, such as propyldiphenylphosphine, can be achieved, since this latter compound is more strongly basic than triphenylphosphine.

As examples of bases that can be mentioned for neutralisation there can be listed sodium and potassium carbonates and hydroxides and ammonium hydroxide. The use of potassium hydroxide or carbonate is preferred since potassium phosphate has high solubility in water.

As examples of solvents that can be present during neutralisation there can be mentioned inert solvents such as toluene, hexane, benzene, and cyclohexane. Alternatively the aldehyde product itself can be used as solvent, e.g. n-butyraldehyde in the case of propylene hydroformylation, or a polymeric condensation product thereof, e.g. "Filmer 351," i.e. a mixture consisting predominantly of trimers of iso-butyraldehyde, nominally of the formulae:

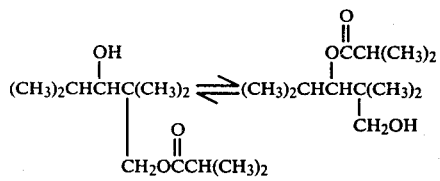

When the aldehyde product itself is used, care must be taken to exclude oxygen or air, as for example by operation under an $N_2$ blanket, in order to prevent oxidation thereof to the corresponding acid since acids are generally catalyst poisons or inhibitors in the hydroformylation reaction.

In order that the invention may be clearly understood and readily carried into effect a preferred process in accordance with the invention will now be described, by way of example only, with reference to the accompanying diagrammatic drawing which is a flow sheet of a hydroformylation plant constructed according to the teachings of the invention.

Referring to the drawing, a stainless steel reactor is provided with a disc impeller 6 having perpendicularly mounted blades which is rotated by means of shaft 7, by a suitable motor (not shown). Located below the impeller 6 is a circular tubular sparger 5 for feeding the α-olefin, such as propylene, and synthesis gas plus the recycle gas. The sparger 5 contains a plurality of holes of sufficient size to provide sufficient gas flow into the liquid body in the vicinity of the impeller 6 to provide the desired amount of the reactants in the liquid body. The reactor is also provided with a steam jacket (not shown) by means of which the contents of the vessel can be brought up to reaction temperature at start-up and with internal cooling coils (not shown).

Vaporous product effluent from the reactor 1 is removed via line 10 to separator 11 where it is passed through a demisting pad 11a therein to return some aldehyde and condensation product to the reactor 1 via line 12 and to prevent potential carry-over of catalyst. The reactor effluent is passed by line 13 to a condenser 14 and then through line 15 to catchpot 16 in which the aldehyde product and any by-product can be condensed out of the off gases. Condensed aldehyde and by-products are removed from the catchpot 16 by line 17. Gaseous materials are passed via line 18 to separator 19 which contains a demisting pad and which is connected to a recycle line 20. Recycle gases are removed by line 21 to line 8 from which a purge through line 22 is pulled to control saturated hydrocarbon content. The remaining and major proportion of the gases can be recycled via line 8 to line 4 into which are fed make-up reactant feeds through lines 2 and 3. The combined total of reactants is fed to the reactor 1. Compressor 26 aids in transporting the recycle gases.

Fresh catalyst solution can be added to the reactor 1 by line 9. The single reactor 1 can of course, be replaced by a plurality of reactors in parallel.

The crude aldehyde product of line 17 can be treated by conventional distillation to separate the various aldehydes and the condensation products. A portion of the crude can be recycled to reactor 1 through line 23 and fed as indicated by broken-line 25 to a point above impeller 6 for the purpose of maintaining the liquid level in reactor 1 if such is required.

A bleed stream of liquid reaction medium is taken by means of line 27 via a cooling zone (not shown) to a mixer section of a conventional mixer-settler 28 to which concentrated phosphoric acid is supplied by means of line 29. An organic phase containing catalytically inactive rhodium species, product aldehyde, "heavies," and triphenylphosphine oxide is removed from the settler section of mixersettler 28 and passed to storage (and eventual work-up for the recovery of dissolved rhodium) by means of line 30. The phosphoric acid extractant phase passes on from settler section of mixer-settler 28 through line 31 to neutralisation stage 32. In neutralisation stage 32 the phosphoric acid phase, which contains most of the catalytically active rhodium as well as most of the triphenylphosphine, present in the reaction medium withdrawn from reactor 1, is diluted somewhat with water which is added by means of line 33 and is then neutralised under an $N_2$ blanket by addition through line 34 of 30% KOH solution in the presence of product aldehyde, e.g. n-butyraldehyde, produced by distillation of crude product aldehyde from line 17. Line 35 indicates an $N_2$ supply line and line 36 represents the product aldehyde supply line. The neutral aqueous phase, which is now essentially rhodium-free, as well as being free from triphenylphosphine, is discarded via line 37. The resulting solution of catalytically active rhodium species and of free triphenylphosphine ligand is recycled to the reactor 1 via line 38.

The invention is further illustrated in the following Example.

EXAMPLE

Hydroformylation of propylene was carried out as described below in a 2,000 ml stainless steel autoclave fitted with a magnetically coupled stirrer and with a sparge tube for supply of the reactants to the autoclave. Provision was made for offtake of an overhead gaseous product whose pressure could be continuously monitored. Accurate temperature control to within ±0.1° C. was achieved by a combination of electrical heating and air cooling, using an internal air cooling coil. The gas feeds to the autoclave were preheated by passage through tube coils immersed in salt baths.

A $CO/H_2/N_2$ mixture was produced by blending the gases upstream from the autoclave, the $CO/H_2/N_2$ ratio being controlled by means of valves on the gas cylinders. This gas mixture was purified by passage through beds of alumina, zinc oxide and copper-impregnated carbon placed in series and maintained at 180° C. The propylene feed was similarly purified.

The autoclave was charged with 500 ml of "Filmer 351," the "trimer" of iso-butyraldehyde, with 130 grams of triphenylphosphine and with 0.6 grams of rhodium carbonyl triphenylphosphine acetylacetonate. The autclave was then flushed with CO/H₂/N₂ mixture and pressurised. The total absolute pressure was 17.6 kg/cm², the partial pressure of H₂ being 4.2 kg/cm², the partial pressure of propylene being 2.8 kg/cm², and the partial pressure of carbon monoxide being 0.7 kg/cm². Calculation of partial pressures was achieved by gas chromatography of the exit gas. The autoclave was then heated to 110° C. and the gas flow rates were adjusted so as to maintain a constant liquid level in the reactor. The liquid level was detected by means of a pair of thermocouples positioned one just above and one just below the desired liquid level. Product butyraldehyde distilled out of the autoclave and was collected in an appropriate water-cooled knock-out pot. The proportions of unreacted propylene, of CO, of H₂ and of propane (formed by hydrogenation in the autoclave) could be determined gas chromatographically. The n-/i- aldehyde ratio could be determined by gas chromatographic analysis of samples collected in the knock-out pot and of the gases exiting the knock-out pot.

The autoclave was operated continuously at 110° C. under the above conditions for 2 days. Under the chosen operating conditions, the n-/iso- aldehyde product ratio was approximately 17:1, the percentage efficiency of conversion of propylene to n-aldehyde about 97% and the percentage conversion of propylene to propane about 1.6%. The catalyst activity was determined at the end of the 2 day period and a value of 100 was arbitrarily assigned to this.

The autoclave was then shut down and its contents cooled. The rhodium concentration was determined to be approximately 200 parts per million. A series of 30 ml aliquots of reactor solution were extracted with varying proportions of "food grade" phosphoric acid and water and then the organic and phosphoric acid layers were analysed for rhodium and triphenylphosphine with the following results:

| Test No. | 1 | 2 | 3 | 4 | 5 |
|---|---|---|---|---|---|
| Conc. Phosphoric acid ml | 8 | 8 | 8 | 8 | 8 |
| Water ml | 0 | 2 | 5 | 10 | 15 |
| (Rh) in organic layer ppm | 1–2 | 2.5 | 13.5 | 42 | 149 |
| (TPP) in organic layer % by wt. | <0.1 | N.D. | N.D. | N.D. | N.D. |

Note: N.D. = not determined.

As discharged from the reactor the liquid reaction medium is yellow. The yellow colour is due to the active catalytic species, it is believed. In the extraction step of Test No. 1 there is obtained a colourless organic layer and a yellow coloured phosphoric acid layer, indicating that the catalytically active species is extracted essentially quantitatively into the acid extractant.

The residue of the reactor solution (850 ml) was extracted with 200 ml "food grade" concentrated phosphoric acid. The resulting phosphoric acid layer was combined with the phosphoric acid layers from Tests Nos. 1 to 5. After dilution with an equal volume of water 500 ml Filmer 351 were added and then the aqueous layer was slowly neutralised with NaOH solution while stirring vigorously. The Filmer solution was separated from the aqueous layer and returned to the autoclave. The resulting charge was then used to hydroformylate propylene under conditions identical to those utilised during the 2 day continuous run. The n-/iso-aldehyde ratio and the percentage conversions of propylene to n-butyraldehyde and to propane were essentially unchanged. The catalyst activity was determined to be 80 compared with 100 during the 2 day continuous run.

What is claimed is:

1. In a process for hydroformylating an α-olefinic compound containing from 2 to about 20 carbon atoms by reaction with carbon monoxide and hydrogen to produce an aldehydic compound or a mixture of aldehydic compounds having one more carbon atom than the α-olefinic compound which comprises:

reacting the α-olefinic compound in a hydroformylation zone with carbon monoxide and hydrogen at a temperature of up to about 160° C. and at a total pressure of up to about 50 kg/cm² absolute in a liquid reaction medium which contains aldehydic product or products, polymeric aldehyde condensation products and a soluble rhodium complex catalyst comprising rhodium in a complex combination with carbon monoxide and a triphenylphosphine and in the presence of excess triphenylphosphine;

the improvement which comprises:
contacting constituents of the liquid reaction medium with a liquid extractant phase comprising at least about 60% by weight phosphoric acid;
separating an organic phase now depleted in rhodium and triphenylphosphine from extractant phase;
recovering rhodium values and triphenylphosphine from separated extractant phase; and
recycling at least one of recovered rhodium values and recovered triphenylphosphine to the hydroformylation zone.

2. A process according to claim 1, wherein the liquid extractant comprises an aqueous phosphoric acid solution which has been pre-saturated with product aldehyde(s).

3. A process according to claim 1, wherein the liquid extractant phase comprises concentrated phosphoric acid.

4. A process according to claim 1, wherein the phosphoric acid is selected from orthophosphoric acid, superphosphoric acid and mixtures thereof.

5. A process according to claim 1, wherein the phosphoric acid comprises so-called "food grade" phosphoric acid.

6. A process according to claim 1, wherein the step of recovering rhodium values and triphenylphosphine from separated extractant phase comprises neutralisation with a base.

7. A process according to claim 7, wherein said neutralisation is effected subsequent to dilution of the extractant phase with water.

8. A process according to claim 7, wherein said neutralisation is effected in the presence of an organic solvent for the active catalytic rhodium species and for the triphenylphosphine.

9. A process according to claim 9, wherein said solvent is selected from product aldehyde, polymeric aldehyde condensation products and mixtures thereof.

* * * * *

UNITED STATES PATENT AND TRADEMARK OFFICE
CERTIFICATE OF CORRECTION

PATENT NO. : 4,242,284
DATED : December 30, 1980
INVENTOR(S) : Norman Harris and Thomas F. Shevels It is certified that error appears in the above—identified patent and that said Letters Patent is hereby corrected as shown below:

Column 4, line 27, delete "be" and substitute --by--.

Column 8, line 21, delete "mixersettler" and substitute --mixer-settler--.

Claim 7, line 55, delete "7" and insert --6--.

Claim 8, line 58, delete "7" and insert --6--.

Claim 9, line 62, delete "9" and insert --8--.

Signed and Sealed this

Seventh Day of April 1981

[SEAL]

Attest:

RENE D. TEGTMEYER

Attesting Officer

Acting Commissioner of Patents and Trademarks